United States Patent
Kuhn et al.

(10) Patent No.: US 6,295,000 B1
(45) Date of Patent: *Sep. 25, 2001

(54) METHOD FOR ASSESSING ACTUATIONS OF THE ACCELERATOR BY A VEHICLE DRIVER TO DETECT NERVOUSNESS

(75) Inventors: Klaus-Peter Kuhn, Plüderhausen; Jochen Strenkert, Stuttgart, both of (DE)

(73) Assignee: Daimler Benz Aktiengesellschaft, Stuttgart (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/118,986

(22) Filed: Jul. 17, 1998

(30) Foreign Application Priority Data

Jul. 18, 1997 (DE) .............................................. 197 30 904

(51) Int. Cl.[7] ................................................... G08B 23/00
(52) U.S. Cl. ......................... 340/576; 340/575; 180/272; 434/258; 701/1
(58) Field of Search ................................. 340/576, 439, 340/438, 441, 575; 180/272; 434/258; 701/1, 70

(56) References Cited

U.S. PATENT DOCUMENTS

| | | | |
|---|---|---|---|
| 4,004,290 | * 1/1977 | Kobayashi et al. | 340/279 |
| 4,641,136 | * 2/1987 | Kowalczyk | 340/903 |
| 5,546,305 | * 8/1996 | Kondo | 340/439 |
| 5,570,087 | * 10/1996 | Lemelson | 340/539 |
| 5,798,695 | * 8/1998 | Metalis et al. | 340/576 |
| 5,835,008 | * 11/1998 | Colemere, Jr. | 340/439 |
| 5,888,074 | * 3/1999 | Staplin et al. | 340/576 |
| 5,900,819 | * 5/1999 | Kyrtsos | 340/576 |

FOREIGN PATENT DOCUMENTS

| | | |
|---|---|---|
| 43 37 957 | 5/1994 | (DE) . |
| 44 01 416 | 7/1995 | (DE) . |
| 414033-A | * 10/1998 | (DE) . |
| 197 30 906 | 1/1999 | (DE) . |
| 197 29 251 | 2/1999 | (DE) . |
| 0 282 387 | 9/1988 | (EP) . |
| 433 603 | 6/1991 | (EP) . |
| 000537811-A1 | * 4/1993 | (EP) . |
| 2 697 884 | 5/1994 | (FR) . |
| 2330185-A | * 10/1997 | (GB) . |

(List continued on next page.)

OTHER PUBLICATIONS

Magazin Forschung und Technik [Research and Technology] der VW AG Fuzzy–Logik für Automatik–Getriebe [Fuzzy Logic for Automatic Transmissions], 1994.**

Die elektronische Steuerung des automatischen Getriebes W5A 330/580 von Mercedes–Bens, by Von Rudolf Rösch und Gerhard Wagner, ATZ Automobiltechnische Zeitschrift 97 (1995), pp. 736–748**.

*Primary Examiner*—Nina Tong
(74) *Attorney, Agent, or Firm*—Kenyon & Kenyon

(57) ABSTRACT

A method for assessing actuations of the accelerator by a vehicle driver to detect the nervousness of the driver, the cumulative path covered by the accelerator, in terms of amount, being evaluated within a predefined time window when the change in velocity is less than a predetermined threshold value and/or the change in position of the accelerator is less than a predetermined threshold value within this time window. Furthermore, alternatively and/or additionally, the number of reversals of the algebraic sign of the time derivation of the accelerator position can be taken into account.

8 Claims, 1 Drawing Sheet

FOREIGN PATENT DOCUMENTS

| | | |
|---|---|---|
| 54-24569 | 8/1979 | (JP) . |
| 6-129521 | 5/1994 | (JP) . |
| 07101271-A * | 4/1995 | (JP) . |
| 07282370-A * | 10/1995 | (JP) . |
| 408161685-A * | 6/1996 | (JP) . |
| 02000111571-A * | 4/2000 | (JP) . |
| 2000326758-A * | 11/2000 | (JP) . |
| WO-009002388-A * | 3/1990 | (WO) .................................. 377/15 |

* cited by examiner

METHOD FOR ASSESSING ACTUATIONS OF THE ACCELERATOR BY A VEHICLE DRIVER TO DETECT NERVOUSNESS

FIELD OF THE INVENTION

The present invention relates to a method for assessing actuations of the accelerator by a vehicle driver.

RELATED TECHNOLOGY

Various methods are known which are used to evaluate the manner in which the vehicle driver actuates the accelerator, in order to differentiate between a steady driving technique and a sporty driving technique. Intermediate steps are also possible in this differentiation, right up to a continuous grading of the driving technique. Such methods are described, e.g. in the magazine *Forschung und Technik* [Research and Technology] of VW AG: *Fuzzy-Logik für Automatikgetriebe* [Fuzzy Logic for Automatic Transmissions], 1994. Such a method is furthermore described in the *Automobiltechnischen Zeitschrift* [Automobile Engineering Periodical] No. 97, 1995 by R. Rösch and G. Wagner: *Die elektronische Steuerung des automatischen Getriebes W5A 330/580 von Mercedes-Benz* [. The Electronic Control of the Automatic Transmission W5A 330/580 of Mercedes-Benz]. When working with these methods, nervous vehicle drivers might accidentally be classified as drivers having a sporty driving technique. The vehicle could then exhibit a performance which is not optimal for this driver.

German Patent Application No. 44 01 416 A1 discloses assessing a driving technique only when a significant change in velocity, which, however, must also not be too great, has occurred within a time window. In this manner, actions owing merely to nervousness of the vehicle driver can be left out of consideration in the evaluation and assessment of the driving technique. As the change in velocity must not be too great, it is furthermore taken into account that it is probably a question of a change in velocity which the vehicle driver is selecting "of his own free will," and which was not forced upon him because of the traffic situation.

It is furthermore disclosed in German Patent Application No. 43 37 957 A1 to evaluate the frequency of a reversal in direction of the adjustment of a throttle valve, and consequently also the frequency of a reversal in direction in response to the actuation of the accelerator of a motor vehicle, in order to detect a possible nervousness of the vehicle driver.

SUMMARY OF THE INVENTION

The present invention provides a method by which nervousness of a vehicle driver can be recognized in which method the cumulative path covered by the accelerator, in terms of amount, is evaluated within a predefined time window when the change in velocity is less than a predetermined threshold value and/or the change in the accelerator position is less than a predetermined threshold value within this time window.

Thus, while in the case of the related art, it was first possible to detect the driving technique when, on the basis of the driving situation, it could be inferred that the action of the vehicle driver was no longer founded on a nervous action, using the method of the present invention, the nervousness of the vehicle driver can be detected in advance. When working with other methods such as an intervention in an engine/transmission management of a vehicle as a function of a steady or sporty driving technique or, for instance, as a function of a spontaneous demand for a dynamic response, it is thus possible to take into consideration early on whether a nervous vehicle driver is present. The actions for the recognition of the driving technique or for the recognition of a spontaneous demand for a dynamic response can thus be appropriately classified early on.

In a further refinement, the instantaneous activity of the vehicle driver is formed from the weighted sum of the criterion used in the method and a further criterion. The further criterion is formed by evaluating how often the algebraic sign of the time derivation of the accelerator position changes, and from this instantaneous activity, the degree of activity of the vehicle driver is furthermore formed and filtered differently depending on the algebraic sign of the change in the instantaneous activity.

Thus, fast changes in the position of the accelerator can be detected particularly advantageously. On the basis of this, a classification can be made with reference to a possible presence of nervousness.

For example, this characteristic number for the degree of activity can be evaluated particularly advantageously during the adaptation of the threshold values for the recognition of a dynamic kickdown.

In yet a further refinement, the activity of the vehicle driver may be ascertained as described above, and furthermore, the driving technique is assessed as lying between steady and sporty. A nervousness of the vehicle driver is recognized when the activity is great, and the driving technique is not assessed as sporty.

In this manner, it can be particularly advantageously evaluated whether an activity of the vehicle driver is purposeful, and is also reflected in corresponding accelerations of the vehicle. This makes it possible to distinguish particularly reliably between a vehicle driver having a sporty driving technique and a nervous driver.

If this evaluation occurs, a nervousness of the vehicle driver then can be determined when the driving technique is not assessed as sporty.

Thus, a vehicle driver having a sporty driving technique is furthermore advantageously prevented from being classified as a nervous driver. This is especially advantageous when the assessment of the driving technique as steady or sporty is not effected by evaluating the actuation of the accelerator, for example, but rather by the automatically adjusting performance of the vehicle, as is described, for instance, in the German Patent 44 01 416 A1. The two criteria of the nervousness of the vehicle driver, on one hand, and the driving technique of the vehicle driver, on the other hand, are then obtained from different data (actuation of the accelerator on one hand, and attained acceleration on the other hand), so that the two criteria to be analyzed are able to be separated well. Otherwise, a recognition of nervousness may have to be forestalled when a sporty driving technique is present, it then becoming difficult, however, to classify whether the actuation of the accelerator at this point due to a sporty driving technique or to the nervousness of the vehicle driver.

A bit may be set in response to a recognized nervousness, and the bit may then be deleted when the conditions for the recognition of the nervousness no longer exist and the position of the accelerator equals 0 (zero, i.e., the accelerator pedal is in an unactuated, or rest position).

Due to this rigorous criterion for the recognition of nervousness, certain interventions in the engine/transmission management can possibly be forestalled Patent Application Nos. 197 30 906.2 and 197 29 251.8, assigned to the present assignee. Both of which are hereby incorporated by reference herein. The co-assigned corresponding U.S. applications, the first entitled "Method for Adjustment of a Throttle Valve" and filed on even date herewith as application Ser. No. 09/118,235 and the second entitled "Method for Recognizing a Spontaneous Demand by a Driver of a Motor Vehicle for a Dynamic Response" and filed on Jul. 9, 1998, as application No. 09/112,895 are hereby incorporated by reference herein.

BRIEF DESCRIPTION OF THE DRAWING

An exemplary embodiment is depicted more precisely in the FIG. 1, which shows schematically the method of the present invention which can be performed by a microprocessor with inputs from a vehicle sensor system and the accelerator.

DETAILED DESCRIPTION

Figure 1:
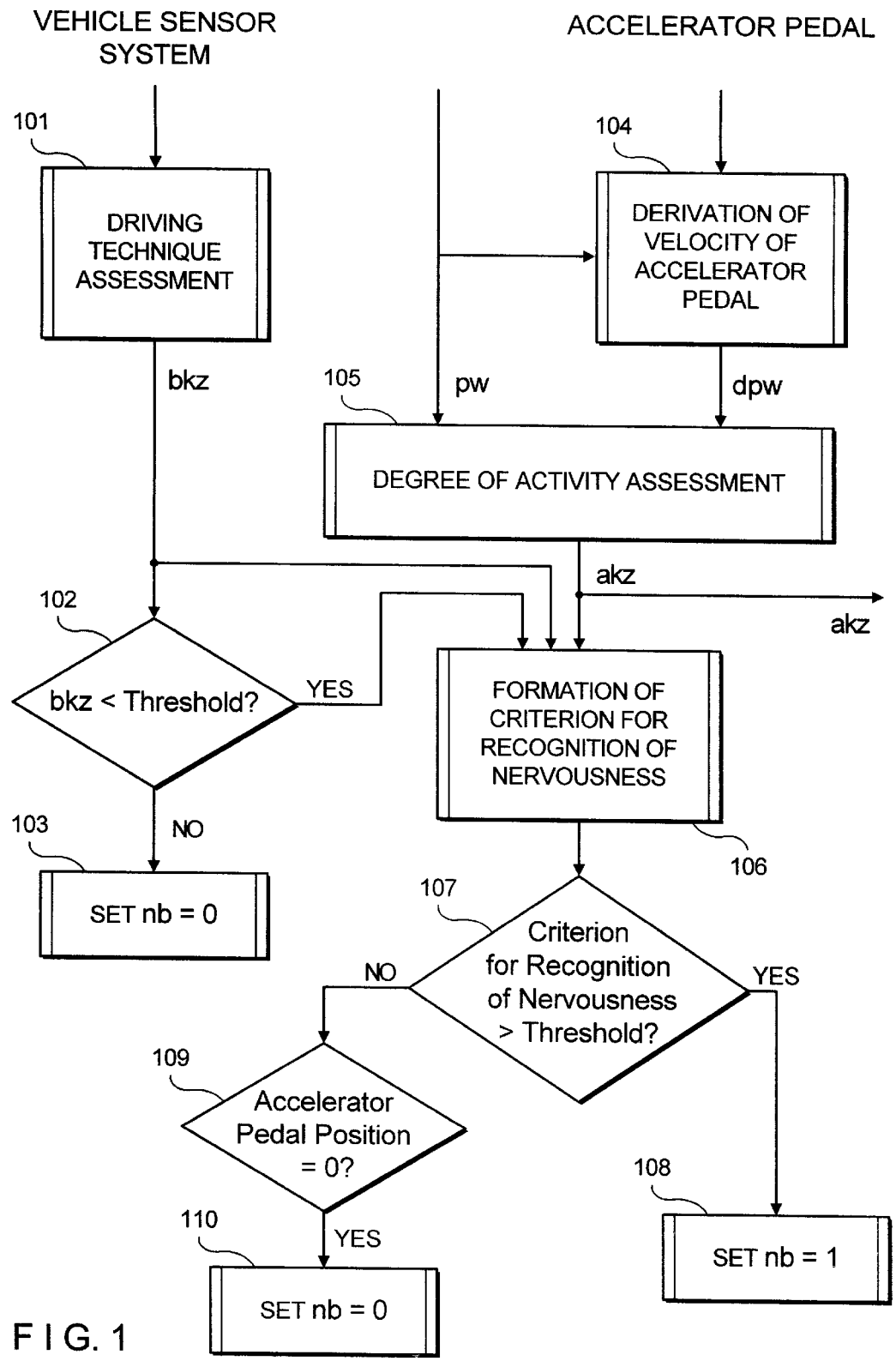

In block 101, the driving technique of the vehicle driver is assessed as steady or as sporty. This can be effected, for example, according to the method described in the German Patent Application No. 44 01 416 A1, which is hereby incorporated by reference herein. Advantageously, in the present application, the acceleration characteristic numeral bkz is used.

In block 102, it is checked whether this acceleration characteristic numeral bkz is smaller than a predefined threshold value.

If this is not the case, and the vehicle driver thus likely has a sporty driving technique, and a transition is made to block 103, in which the nervousness bit nb is set to 0.

If it was determined in block 102 that the acceleration characteristic numeral is smaller than the threshold value, a transition is made to block 106. In block 106, the criterion is formed, on the basis of which, the nervousness is intended to be recognized. To that end, if the condition from block 102 is fulfilled, an index of the correlation from acceleration characteristic numeral bkz and degree of activity akz is formed.

The degree of activity akz is ascertained in block 105. A signal pw representing the position of the accelerator, and a signal dpw representing the time derivation of this signal are supplied to this block. The time derivation, i.e., the velocity of the accelerator, is obtained in block 104.

The criteria for recognizing nervousness of the vehicle driver are formed in block 105. The first criterion is computed from the cumulative path, in terms of amount, the accelerator has covered within a time window. In this context, no significant change in velocity and/or change in the position of the accelerator may take place within this time window. Meant by this is a change in the accelerator position which, given a movement without a movement reversal, exceeds a certain amount. On the other hand, the cumulative path will turn out to be comparatively great precisely in the case of a vehicle driver to be classified as nervous. The cumulative path is, of course, advantageously corrected of signal noise.

In block 105, a further criterion is formed on the basis of the number of reversals of the algebraic sign of the change in the accelerator position as a function of time within the time window considered.

Likewise determined in block 105 from these two criteria is the instantaneous activity as the weighted sum of the scaled characteristic numbers. The degree of activity akz is computed from the scaled, instantaneous activity, filtered differently depending on the algebraic sign of the change. The activity number, similar to the acceleration characteristic number bkz, is available as a criterion for interventions in the engine/transmission management, for example.

In block 107, the criterion formed in block 106 is analyzed with regard to whether it exceeds a predetermined threshold.

If this is the case, a transition is made to block 108, in which nervousness bit nb is set to 1.

If this is not the case, a transition is made to block 109, in which it is further checked whether the accelerator stands at 0. If this is the case, in step 110, nervousness bit nb is set to 0.

In the result, a nervousness bit nb is thus yielded which represents a sharp separation as to whether the vehicle driver is nervous (yes/no). In addition, a further characteristic quantity is available which reflects the degree of individual activity akz. This information can be used, for example, in the adaptation of accelerator characteristics and/or gear shift lines, so that, by a calm driving strategy to this effect, the greatest possible travel comfort and good vehicle handling, accompanied by good consumption, can be offered to even a nervous vehicle driver. The same also holds true, for example, for the coordination of accelerator/throttle valve or injection quantity, which can be rendered indirectly by an appropriate signal processing, e.g. through a suitable low-pass filtering.

What is claimed is:

1. A method for assessing actuations of an accelerator pedal by a driver of a vehicle to detect a nervous driver condition comprising the steps of:

evaluating a cumulative amount traveled by the accelerator pedal within a predefined time period when at least one of a change in velocity of the vehicle is less than a first predetermined threshold value within the predefined time period and a change in a position of the accelerator pedal is less than a second predetermined threshold value within the predefined time period; and using at least the cumulative amount traveled so as to detect the nervous driver condition.

2. The method as recited in claim 1 further comprising the steps of:

evaluating a number of times an algebraic sign of a time differentiation of the position of the accelerator pedal changes so as to form a further criterion;

forming a weighted sum as a function of the cumulative amount traveled and as a function of the further criterion; and forming a degree of activity of the vehicle driver as a function of the weighted sum.

3. The method as recited in claim 2 further comprising filtering the degree of activity as a function of the algebraic sign.

4. The method as recited in claim 2 further comprising the step of assessing a driving technique of the driver as steadier or sportier, and recognizing the nervous driver condition when the degree of activity exceeds a certain amount and the driving technique is not assessed as sportier.

5. The method as recited in claim 1 further comprising the steps of:

determining an activity of the vehicle driver;

assessing a driving technique of the driver as steadier or sportier; and assessing that the nervous driver condition exists when the activity exceeds a certain amount and the driving technique is not assessed as sportier.

6. The method as recited in claim 1 further comprising the step of setting a bit when the nervous driver condition is recognized and deleting the bit when conditions for the recognition of the nervous driver condition no longer exist and the position of the accelerator pedal equals zero.

7. A method for assessing actuations of an accelerator pedal by a driver of a vehicle to detect a nervous driver condition comprising the steps of:

evaluating a cumulative amount traveled by the accelerator pedal within a predefined time period when a change in velocity of the vehicle is less than a predetermined threshold value within the predefined time period; and using at least the cumulative amount traveled so as to detect the nervous driver condition.

8. A method for assessing actuations of an accelerator pedal by a driver of a vehicle to detect a nervous driver condition comprising the steps of:

evaluating a cumulative amount traveled by the accelerator pedal within a predefined time period when a change in a position of the accelerator pedal is less than a predetermined threshold value within the predefined time period; and using at least the cumulative amount traveled so as to detect the nervous driver condition.

\* \* \* \* \*

UNITED STATES PATENT AND TRADEMARK OFFICE
CERTIFICATE OF CORRECTION

PATENT NO. : 6,295,000 B1
DATED : September 25, 2001
INVENTOR(S) : Kuhn et al.

It is certified that error appears in the above-identified patent and that said Letters Patent is hereby corrected as shown below:

<u>Title page,</u>
Item [56], OTHER PUBLICATONS, "Mercedes-" change "Bens" to -- Benz --;

<u>Column 2,</u>
Line 67, after "forestalled" insert -- when nervousness has been recognized. This is described in detail in German --.

Signed and Sealed this

Twentieth Day of August, 2002

*Attest:*

*Attesting Officer*

JAMES E. ROGAN
*Director of the United States Patent and Trademark Office*